US011969545B2

(12) United States Patent
Holt et al.

(10) Patent No.: US 11,969,545 B2
(45) Date of Patent: Apr. 30, 2024

(54) LIQUID FEED SYSTEMS FOR AN AEROSOL DELIVERY DEVICE

(71) Applicant: RAI Strategic Holdings, Inc., Winston-Salem, NC (US)

(72) Inventors: Justin Dakota Holt, Stokesdale, NC (US); Andries Don Sebastian, Kathleen, GA (US); Stephen B. Sears, Siler City, NC (US); Vahid Hejazi, Concord, NC (US); Rajesh Sur, Winston-Salem, NC (US); Cassidy S. McMahan, Pfafftown, NC (US); S. Keith Cole, Advance, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 565 days.

(21) Appl. No.: 17/108,628

(22) Filed: Dec. 1, 2020

(65) Prior Publication Data

US 2022/0168513 A1 Jun. 2, 2022

(51) Int. Cl.
*A61M 15/00* (2006.01)
*A61M 15/06* (2006.01)

(52) U.S. Cl.
CPC ...... *A61M 15/009* (2013.01); *A61M 15/0085* (2013.01); *A61M 15/06* (2013.01); *A61M 2205/0211* (2013.01)

(58) Field of Classification Search
CPC .......... A24F 40/05; A24F 40/10; A24F 40/48; A61M 15/06; A61M 11/00
See application file for complete search history.

(56) References Cited

U.S. PATENT DOCUMENTS 5,996,903 A 12/1999 Asai et al.
8,998,483 B2 4/2015 Friend et al.
(Continued)

FOREIGN PATENT DOCUMENTS

CN 206423575 8/2017
EE 3272237 1/2018
(Continued)

OTHER PUBLICATIONS

Merriam-Webster, "Integrate" definition, downloaded to pdf on Mar. 15, 2023; https://journals.plos.org/plosone/article?id=10.1371/journal.pone.0050320 (Year: 2023).*
(Continued)

*Primary Examiner* — Valerie L Woodward
(74) *Attorney, Agent, or Firm* — WOMBLE BOND DICKINSON (US) LLP

(57) ABSTRACT

The present disclosure provides an aerosol delivery device that includes a housing including a power source and a control component, a reservoir configured to contain a liquid composition, a liquid delivery component including a micropump, and an atomizing assembly including a vibrating component and a mesh plate. The micropump is configured to be controlled by the control component to deliver at least a portion of the liquid composition to the atomizing assembly, the atomizing assembly is configured to be controlled by the control component to vaporize the portion of the liquid composition to generate an aerosol, and the micropump and the atomizing assembly are integrated together using a common element. In another implementation, the micropump comprises a biomimetic micropump. In some implementations, the biomimetic micropump may include a xylem model structure and a leaf model structure.

14 Claims, 10 Drawing Sheets

(56) References Cited

U.S. PATENT DOCUMENTS

| | | |
|---|---|---|
| 9,770,055 B2 | 9/2017 | Cameron et al. |
| 9,848,648 B2 | 12/2017 | Memari et al. |
| 9,867,398 B2 | 1/2018 | Guo et al. |
| 9,936,737 B2 | 4/2018 | Cameron et al. |
| 9,962,507 B2 | 5/2018 | Germinario et al. |
| 10,004,259 B2 | 6/2018 | Sebastian et al. |
| 2006/0196518 A1 | 9/2006 | Hon |
| 2008/0084134 A1 | 4/2008 | Morita et al. |
| 2009/0151717 A1 | 6/2009 | Bowen et al. |
| 2013/0213419 A1 | 8/2013 | Tucker et al. |
| 2013/0319404 A1 | 12/2013 | Feriani et al. |
| 2014/0238423 A1 | 8/2014 | Tucker et al. |
| 2014/0261487 A1 | 9/2014 | Chapman et al. |
| 2015/0034103 A1 | 2/2015 | Hon |
| 2015/0101606 A1 | 4/2015 | White |
| 2015/0117841 A1 | 4/2015 | Brammer et al. |
| 2015/0238423 A1 | 8/2015 | Wertz et al. |
| 2015/0245669 A1 | 9/2015 | Cadieux et al. |
| 2016/0213866 A1 | 7/2016 | Tan |
| 2016/0271347 A1 | 9/2016 | Raichman |
| 2016/0338407 A1* | 11/2016 | Kerdemelidis ......... A24F 40/60 |
| 2016/0366946 A1 | 12/2016 | Murison et al. |
| 2017/0042241 A1 | 2/2017 | Murison et al. |
| 2017/0064997 A1 | 3/2017 | Murison et al. |
| 2017/0157341 A1 | 6/2017 | Pandya et al. |
| 2017/0238608 A1 | 8/2017 | Matsumoto et al. |
| 2017/0303594 A1 | 10/2017 | Cameron et al. |
| 2017/0368273 A1 | 12/2017 | Rubin |
| 2018/0038838 A1 | 2/2018 | Karancsi et al. |
| 2018/0090923 A1 | 3/2018 | Li et al. |
| 2018/0153217 A1 | 6/2018 | Liu et al. |
| 2018/0161525 A1 | 6/2018 | Liu et al. |
| 2018/0169691 A1 | 6/2018 | Macloughlin et al. |
| 2018/0289076 A1 | 10/2018 | Manca et al. |
| 2018/0325169 A1 | 11/2018 | Guo et al. |
| 2019/0014819 A1* | 1/2019 | Sur ..................... A24F 40/05 |
| 2019/0125987 A1 | 5/2019 | Germinario et al. |
| 2020/0276398 A1 | 9/2020 | Hebrank et al. |
| 2020/0367553 A1 | 11/2020 | Hejazi |

FOREIGN PATENT DOCUMENTS

| | | |
|---|---|---|
| EP | 1 602 414 A2 | 12/2005 |
| EP | 3228345 | 10/2017 |
| EP | 3278678 | 2/2018 |
| EP | 3287019 | 2/2018 |
| EP | 3298912 | 3/2018 |
| EP | 3305104 | 4/2018 |
| EP | 3 501 309 A1 | 6/2019 |
| EP | 3 370 551 B1 | 12/2020 |
| WO | WO2016165055 | 10/2016 |
| WO | WO2017051181 | 3/2017 |
| WO | WO2017063256 | 4/2017 |
| WO | WO2017149165 | 9/2017 |
| WO | WO2017175218 | 10/2017 |
| WO | WO2017201710 | 11/2017 |
| WO | WO2017201716 | 11/2017 |
| WO | WO2017202014 | 11/2017 |
| WO | WO2017206022 | 12/2017 |
| WO | WO2017206480 | 12/2017 |
| WO | WO2017215221 | 12/2017 |
| WO | WO2018000469 | 1/2018 |
| WO | WO2018000756 | 1/2018 |
| WO | WO2018000760 | 1/2018 |
| WO | WO2018000761 | 1/2018 |
| WO | WO2018000829 | 1/2018 |
| WO | WO2018001105 | 1/2018 |
| WO | WO2018001106 | 1/2018 |
| WO | WO2018023890 | 2/2018 |
| WO | WO2018032553 | 2/2018 |
| WO | WO2018040380 | 3/2018 |
| WO | WO2018053955 | 3/2018 |
| WO | WO2018058883 | 4/2018 |
| WO | WO2018058884 | 4/2018 |
| WO | WO2018095312 | 5/2018 |

OTHER PUBLICATIONS

Li et al., "A Microfluidic Pump/Valve Inspired by Xylem Embolism and Transpiration in Plants", (Nov. 29, 2012), PLoS One 7(11): e50320, pp. 1-5; https://journals.plos.org/plosone/article?id=10.1371/journal.pone.0050320 (Year: 2023).*

Li et al. "A micropump based on water potential difference in plants", (Aug. 12, 2011), Microfluid Nanofluid 11, pp. 717-724; https://doi.org/10.1007/s10404-011-0837-y (Year: 2023).*

Lamb et al. "A synthetic leaf: the biomimetic potential of graphene oxide", (Mar. 26, 2015), SPIE Digital Library vol. 9429, Bioinspiration, Biomimetics, and Bioreplication 2015, 942915; https://doi.org/10.1117/12.2086567 (Year: 2023).*

Liu et al, "Evaporation characteristics of micropores in biomimetic micropump", (Jan. 1, 2014) Micro & Nano Letters, 9: 41-45. https://doi.org/10.1049/mnl.2013.0554 (Year: 2023).*

Ding et al., "Surface acoustic wave microfluidics", The Royal Society of Chemistry, Issue 18, Jul. 2013, pp. 3626-3649. Retrieved from the Internet: <DOI: 10.1039/c3lc5036le>.

Yeo & Friend, "Ultrafast microfluidics using surface acoustic waves", American Institute of Physics, vol. 3, Issue 1, 2009, pp. 1-23. Retrieved from the Internet <URL: https://aip.scitation.org/doi/10.1063/1.3056040> <DOI: 10.1063/1.3056040>.

Qi et al., "Miniature inhalation therapy platform using surface acoustic wave microfluidic atomization", The Royal Society of Chemistry, Issue 15, May 2009, pp. 2184-2193. Retrieved from the Internet <URL: https://pubs.rsc.org/en/content/articlelanding/2009/LC/b903575c#!divAbstract> <DOI: 10.1039/b903575c>.

Ariyakul & Nakamoto, "Olfactory Display Using a Miniaturized Pump and a SAW Atomizer for Presenting Low-volatile Scents", IEEE Virtual Reality, Singapore, Mar. 2011, pp. 193-194.

Olszewski et al., "A silicon-based MEMS vibrating mesh nebulizer for inhaled drug delivery", Procedia Engineering, vol. 168, 2016, pp. 1521-1524. Retrieved from the Internet <URL: https://www.sciencedirect.com/science/article/pii/S1877705816337729?via%3Dihub> <DOI: 10.1016/j.proeng.2016.11.451>.

Hawkins & Feng, "Vibrating Mesh Nebulizer Reference Design", Microchip Technology Inc., 2016-2017, pp. 1-50.

Kesten et al., "Development of a novel digital breath-activated inhaler: Initial particle size characterization and clinical testing", Pulmonary Pharmacology & Therapeutics, vol. 53, Carlsbad, California, USA, Dec. 2018, pp. 27-32. Retrieved from the Internet <URL: https://www.sciencedirect.com/science/article/pii/S1094553918301251?via%3Dihub> <DOI: 10.1016/j.pupt.2018.08.007>.

Amador, G., et al., "Thermocapillary-driven fluid flow within microchannels", Physical Intelligence Department, Max Planck Institute for Intelligent Systems, Stuttgart, Germany, Feb. 5, 2018, pp. 1-22.

Kooij, S., et al., "Size distributions of droplets produced by ultrasonic nebulizers", Scientific Reports, Apr. 16, 2019, pp. 1-8, Retrieved from the Internet: <URL: www.https://doi.org/10.1038/s41598-019-42599-8>.

Hillyard, S., "Sensing Meets Separation: Water Transport Across Biological Membranes", in: *Biomimetic Membranes for Sensor and Separation Applications* (Springer, Jan. 2, 2012), pp. 17-18.

YouTube video clip entitled "Controlling flow in microfluidic part with gradient coatings (Surnetics-LasX collaboration)", uploaded on Jan. 29, 2014 by user "Surnetics". Retrieved from the Internet: <URL: youtube.com/watch?v=TL4dlo2Cwpc&feature=youtu.be>.

"Tesla's Valvular Conduit", Fluid Power Journal, 9 pages. Retrieved from the Internet: <URL: web.archive.org/web/20170113033316/https:/fluidpowerjournal.com/2013/10/teslas-conduit/>.

De Vries, S.F., et al., "Design and operation of a Tesla-type valve for pulsating heat pipes", in: International Journal of Heat and Mass Transfer, vol. 105, Feb. 2017, 33 pages. Retrieved from the Internet: <URL: https://doi.org/10.1016/j.ijheatmasstransfer.2016.09.062>.

Piyasena, M., et al., "Electroosmotically driven microfluidic actuators", in: Sensors and Actuators B: Chemical, vol. 141, Issue 1, Aug. 18, 2009, pp. 263-269. Retrieved from the Internet: <URL: https://doi.org/10.1016/j.snb.2009.05.014>.

(56) References Cited

OTHER PUBLICATIONS

International Search Report in the corresponding International Patent Application No. PCT/IB2021/061087, dated Mar. 3, 2022, 3 pages.

* cited by examiner

LIQUID FEED SYSTEMS FOR AN AEROSOL DELIVERY DEVICE

TECHNOLOGICAL FIELD

The present disclosure relates to aerosol delivery devices, and more particularly to an aerosol delivery device that includes an atomizing assembly that may utilize electrical power to vaporize a liquid composition, which may include an aerosol precursor composition, for the production of an aerosol. In various implementations, the liquid composition, which may incorporate materials and/or components that may be made or derived from tobacco or otherwise incorporate tobacco or other plants, may include natural or synthetic components including flavorants, and/or may include one or more medicinal components, is vaporized by the atomizing assembly to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered sources referenced by brand name and commercial source in U.S. Pat. App. Pub. No. 2015/0216232 to Bless et al., which is incorporated herein by reference in its entirety.

It would be desirable, however, to provide an aerosol delivery device with enhanced functionality. In this regard, it is desirable to provide an aerosol delivery with advantageous features.

BRIEF SUMMARY

The present disclosure relates to aerosol delivery devices, methods of forming such devices, and elements of such devices. The present disclosure includes, without limitation, the following example implementations:

Example Implementation 1: An aerosol delivery device comprising a housing including a power source and a control component, a reservoir configured to contain a liquid composition, a liquid delivery component comprising a micropump, and an atomizing assembly comprising a vibrating component and a mesh plate, wherein the micropump is configured to be controlled by the control component to deliver at least a portion of the liquid composition to the atomizing assembly, wherein the atomizing assembly is configured to be controlled by the control component to vaporize the portion of the liquid composition to generate an aerosol, and wherein the micropump and the atomizing assembly are integrated together using a common element.

Example Implementation 2: The aerosol delivery device of Example Implementation 1, or any combination of preceding example implementations, wherein the micropump comprises a piezoelectric micropump, wherein the vibrating component comprises a piezoelectric vibrating component, and wherein piezoelectric micropump and the piezoelectric vibrating component are integrated together using a common piezoelectric element.

Example Implementation 3: The aerosol delivery device of any one of Example Implementations 1-2, or any combination of preceding example implementations, wherein a vibrating frequency of the piezoelectric micropump is synchronized with a vibrating frequency of the piezoelectric vibrating component.

Example Implementation 4: The aerosol delivery device of any one of Example Implementations 1-3, or any combination of preceding example implementations, wherein the vibrating component comprises a piezoelectric ring affixed to and substantially surrounding the mesh plate.

Example Implementation 5: The aerosol delivery device of any one of Example Implementations 1-4, or any combination of preceding example implementations, wherein the mesh plate of the vibrating assembly is substantially flat.

Example Implementation 6: The aerosol delivery device of any one of Example Implementations 1-5, or any combination of preceding example implementations, wherein at least a portion of the mesh plate is convex with respect to the respective reservoir.

Example Implementation 7: An aerosol delivery device comprising a housing including a power source and a control component, a reservoir configured to contain a liquid composition, a liquid delivery component comprising micropump, and an atomizing assembly comprising a vibrating component and a mesh plate, wherein the micropump is configured to be controlled by the control component to deliver at least a portion of the liquid composition to the atomizing assembly, and wherein the atomizing assembly is configured to be controlled by the control component to vaporize the portion of the liquid composition to generate an aerosol, and wherein the micropump comprises a biomimetic micropump.

Example Implementation 8: The aerosol delivery device of Example Implementation 7, or any combination of preceding example implementations, wherein the biomimetic micropump comprises a xylem model component and a leaf model component.

Example Implementation 9: The aerosol delivery device of any one of Example Implementations 7-8, or any combination of preceding example implementations, wherein the leaf model component is integrated with the vibrating component of the atomizing assembly.

Example Implementation 10: The aerosol delivery device of any one of Example Implementations 7-9, or any combination of preceding example implementations, wherein the xylem model component comprises one or both of a ceramic material or a controllable material.

Example Implementation 11: The aerosol delivery device of any one of Example Implementations 7-10, or any combination of preceding example implementations, wherein the leaf model component comprises a microperforated structure.

Example Implementation 12: The aerosol delivery device of any one of Example Implementations 7-11, or any combination of preceding example implementations, wherein the leaf model component comprises a portion of the atomizing assembly.

Example Implementation 13: The aerosol delivery device of any one of Example Implementations 7-12, or any combination of preceding example implementations, wherein the leaf model component comprises the mesh plate.

Example Implementation 14: The aerosol delivery device of any one of Example Implementations 7-13, or any combination of preceding example implementations, wherein the vibrating component comprises a piezoelectric ring affixed to and substantially surrounding the mesh plate.

Example Implementation 15: The aerosol delivery device of any Example Implementation 7-14, or any combination of preceding example implementations, wherein the mesh plate of the vibrating assembly is substantially flat.

Example Implementation 16: The aerosol delivery device of any one of Example Implementations 7-15, or any combination of preceding example implementations, wherein at least a portion of the mesh plate is convex with respect to the respective reservoir.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

BRIEF DESCRIPTION OF THE DRAWINGS

In order to assist the understanding of aspects of the disclosure, reference will now be made to the appended drawings, which are not necessarily drawn to scale and in which like reference numerals refer to like elements. The drawings are provided by way of example to assist understanding of aspects of the disclosure, and should not be construed as limiting the disclosure.

DETAILED DESCRIPTION

Figure 1:
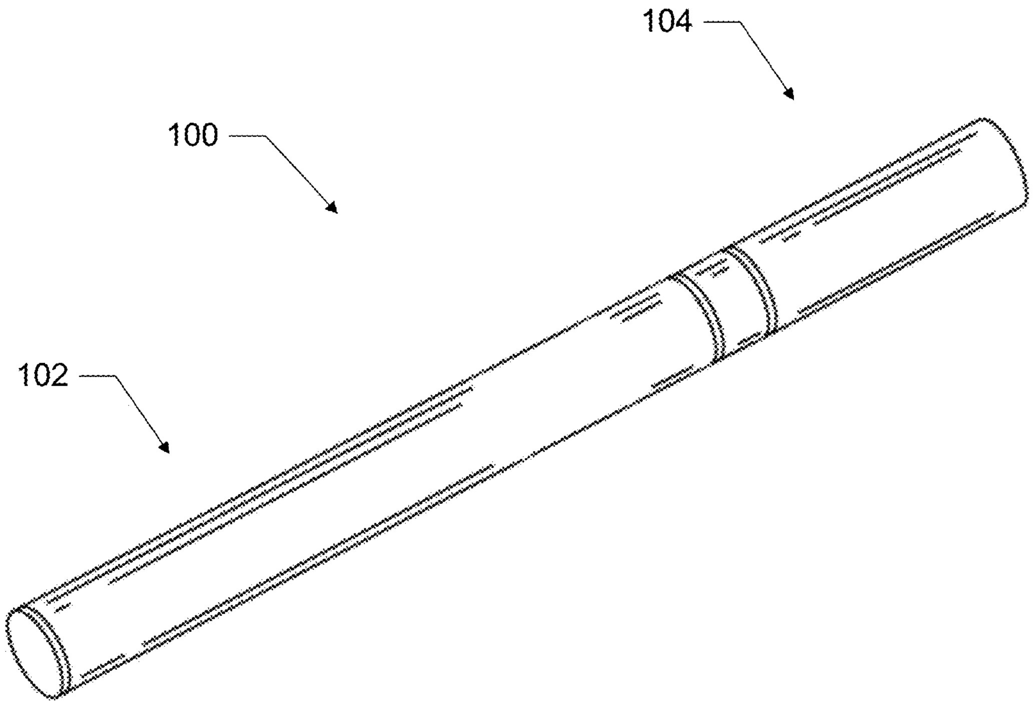
FIG. 1 is a perspective view of an aerosol delivery device, according to an example implementation of the present disclosure.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms “a”, “an”, “the”, include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to vaporize a material (preferably without combusting the material to any significant degree and/or without significant chemical alteration of the material) to form an inhalable substance; and components of such devices have the form of articles that most preferably are sufficiently compact to be considered hand-held devices. That is, use of components of some aerosol delivery devices does not result in the production of smoke—i.e., from by-products of combustion or pyrolysis of tobacco, but rather, use of those preferred systems results in the production of vapors resulting from vaporization of an aerosol precursor composition. In some examples, components of aerosol delivery devices may be characterized as electronic cigarettes, and those electronic cigarettes most preferably incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use the device much like a smoker employs a traditional type of smoking article, draw on one end of that device for inhalation of aerosol produced by that device, take or draw puffs at selected intervals of time, and the like.

Aerosol delivery devices of the present disclosure also may be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power, such as by controlling electrical current flow the power source to other components of the article—e.g., a microcontroller or microprocessor), an atomizing assembly, a liquid composition (e.g., commonly an aerosol precursor composition liquid capable of yielding an aerosol, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated may be withdrawn therefrom upon draw).

Alignment of the components within the aerosol delivery device may be variable. In specific embodiments, the aerosol precursor composition may be located between two opposing ends of the device (e.g., within a reservoir of a cartridge, which in certain circumstances is replaceable and disposable or refillable). Other configurations, however, are not excluded. Generally, the components are configured relative to one another so that energy from the atomizing assembly vaporizes the aerosol precursor composition (as well as one or more flavorants, medicaments, or the like that may likewise be provided for delivery to a user) and forms an aerosol for delivery to the user. When the atomizing assembly vaporizes the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

More specific formats, configurations and arrangements of components within the aerosol delivery devices of the present disclosure will be evident in light of the further disclosure provided hereinafter. Additionally, the selection and arrangement of various aerosol delivery device components may be appreciated upon consideration of the commercially available electronic aerosol delivery devices, such as those representative products referenced in the background art section of the present disclosure.

FIG. 1 illustrates an aerosol delivery device, according to an example implementation of the present disclosure. In particular, FIG. 1 illustrates a perspective schematic view of an aerosol delivery device 100 comprising a cartridge 104 and a control unit 102. As depicted in the figure, the cartridge 104 may be permanently or detachably aligned in a functioning relationship with the control unit 102. In some implementations, for example, the cartridge and the control unit may comprise a single, unitary part, whereas in other implementations (such as the depicted implementation), a connection therebetween may be releasable such that, for example, the control unit may be reused with one or more additional cartridges that may be disposable and/or refillable. In various implementations, a variety of different means of engagement may be used to couple a cartridge and a control unit together. For example, in some implementations the cartridge and the control unit may be coupled via one or more of a snap fit engagement, a press fit engagement, a threaded engagement, or a magnetic engagement. It should be noted that the components depicted in this and the other figures are representative of the components that may be present in a control unit and/or cartridge and are not intended to limit the scope of the control unit and/or cartridge components that are encompassed by the present disclosure.

Figure 2:
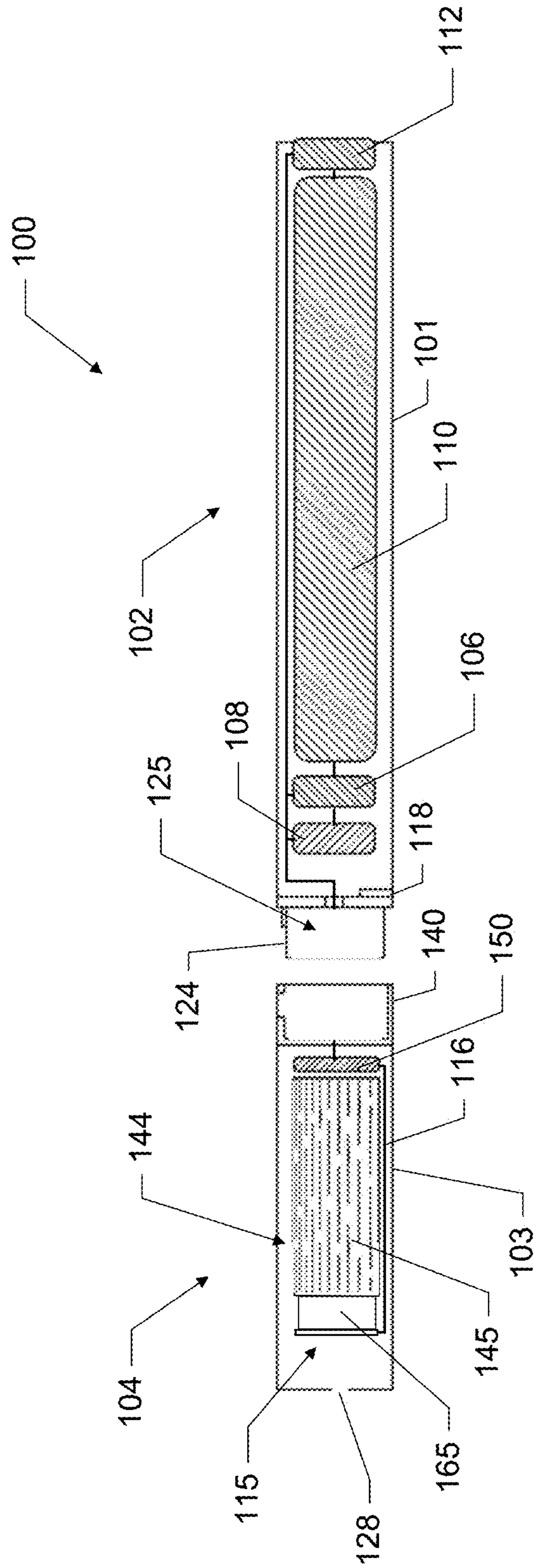
FIG. 2 illustrates a side schematic view of an aerosol delivery device, according to an example implementation of the present disclosure.

FIG. 2 illustrates a side schematic view of the aerosol delivery device 100. As depicted, the cartridge 104 and control unit 102 of FIG. 1 are shown in a de-coupled configuration. In various implementations, the aerosol delivery device 100 may have a variety of different shapes. For example, in some implementations (such as the depicted implementation) the aerosol delivery device 100 may be substantially rod-like or substantially tubular shaped or substantially cylindrically shaped. In other implementations, however, other shapes and dimensions are possible (e.g., rectangular, oval, hexagonal, prismatic, regular or irregular polygon shapes, disc-shaped, cube-shaped, multifaceted shapes, or the like). In still other implementations, the cartridge and the control unit may each have different shapes. It should be noted for purposes of the present disclosure that the term "substantially" should be understood to mean approximately and/or within a certain degree of manufacturing tolerance as would be understood by one skilled in the art.

In the depicted implementation, the control unit 102 and the cartridge 104 include components adapted to facilitate mechanical engagement therebetween. Although a variety of other configurations are possible, the control unit 102 of the depicted implementation includes a coupler 124 that defines a cavity 125 therein. Likewise, the cartridge 104 includes a base 140 adapted to engage the coupler 124 of the control unit 102. A coupler and a base that may be useful according to the present disclosure are described in U.S. Pat. App. Pub. No. 2014/0261495 to Novak et al., the disclosure of which is incorporated herein by reference in its entirety.

It should be noted, however, that in other implementations various other structures, shapes, and/or components may be employed to couple the control unit and the cartridge. For example, in some implementations the control unit and cartridge may be coupled together via an interference or press fit connection such as, for example, implementations wherein the control body includes a chamber configured to receive at least a portion of the cartridge or implementations wherein the cartridge includes a chamber configured to receive at least a portion of the control unit. In other implementations, the cartridge and the control unit may be coupled together via a screw thread connection. In still other implementations, the cartridge and the control unit may be coupled together via a bayonet connection. In still other implementations, the cartridge and the control unit may be coupled via a magnetic connection. In various implementations, once coupled an electrical connection may be created between the cartridge and the control unit so as to electrically connect the cartridge (and components thereof) to the battery and/or via the control component of the control unit. Such an electrical connection may exist via one or more components of the coupling features. In such a manner, corresponding electrical contacts in the cartridge and the control unit may be substantially aligned after coupling to provide the electrical connection.

In specific implementations, one or both of the control unit 102 and the cartridge 104 may be referred to as being disposable or as being reusable. For example, in some implementations the control unit may have a replaceable battery or a rechargeable battery and thus may be combined with any type of recharging technology, including connection to a wall charger, connection to a car charger (e.g., cigarette lighter receptacle, USB port, etc.), connection to a computer, any of which may include a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, or wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

As illustrated in the figure, the control unit 102 may be formed of a control unit housing 101 that includes a control component 106 (e.g., a printed circuit board (PCB), an integrated circuit, a memory component, a microcontroller, or the like), a flow sensor 108, a power source 110 (e.g., one or more batteries), and a light-emitting diode (LED) 112, which components may be variably aligned. Some example types of electronic components, structures, and configurations thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference in their entireties. Some examples of batteries that may be applicable to the present disclosure are described in U.S. Pat. App. Pub. No. 2010/0028766 to Peckerar et al., the disclosure of which is incorporated herein by reference in its entirety. In some implementations, further indicators (e.g., a haptic feedback component, an audio feedback component, or the like) may be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties. It should be understood that in various implementations not all of the illustrated elements may be required. For example, in some implementations an LED may be absent or may be replaced with a different indicator, such as a vibrating indicator. Likewise, a flow sensor may be replaced with a manual actuator, such as, for example, one or more manually actuated push buttons.

In the depicted implementation, the cartridge 104 may be formed of a cartridge housing 103, which may define a reservoir 144, which in the depicted implementation is configured to contain a liquid composition 145. In some implementations, the reservoir may be part of the cartridge housing (such as, for example, comprising a molded feature of the cartridge housing), while in other implementations, the reservoir may comprise a separate part. In some implementations, the reservoir may be disposable. In other implementations, the reservoir may be refillable. In various implementations, the reservoir may be configured to contain a liquid composition, a semisolid composition, and/or a gel composition, which may comprise an aerosol precursor composition. Some examples of types of substrates, reservoirs, or other components for supporting a liquid composition are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety.

In some implementations, the reservoir may be made of a polymeric material that, in further implementations, may be at least partially transparent or translucent. In some implementations, such materials, may include, but need not be limited to, polycarbonate, acrylic, polyethylene terephthalate (PET), amorphous copolyester (PETG), polyvinyl chloride (PVC), liquid silicone rubber (LSR), cyclic olefin copolymers, polyethylene (PE), ionomer resin, polypropylene (PP), fluorinated ethylene propylene (FEP), styrene methyl methacrylate (SMMA), styrene acrylonitrile resin (SAN), polystyrene, acrylonitrile butadiene styrene (ABS), and combinations thereof. Other materials may include, for example, biodegradable polymers such as, but not limited to, polylactic acid (PLA), polyhydroxyalkanoates (PHA's), and polybutylene succinate (PBS). In some implementations, the reservoir may be made of other material that may be at least partially transparent or translucent. Such materials may include, for example, glass or ceramic materials.

In some implementations, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference in its entirety. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine, USP/EP nicotine, etc.). In other implementations, non-tobacco materials alone may form the aerosol precursor composition. In some implementations, the aerosol precursor composition may include tobacco-extracted nicotine with tobacco or non-tobacco flavors and/or non-tobacco-extracted nicotine with tobacco or non-tobacco flavors.

In the depicted implementation, the liquid composition, sometimes referred to as an aerosol precursor composition or a vapor precursor composition or "e-liquid", may comprise a variety of components, which may include, by way of example, a polyhydric alcohol (e.g., glycerin, propylene glycol, or a mixture thereof), nicotine, tobacco, tobacco extract, and/or flavorants. Representative types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B. V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor composition that is incorporated within the aerosol delivery system is such that the aerosol generating device provides acceptable sensory and desirable performance characteristics. For example, sufficient amounts of aerosol forming material (e.g., glycerin and/or propylene glycol) may be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In the some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 1% nicotine. For example, in some implementations the percentage nicotine in the water-based liquid may be in the inclusive range of approximately 0.1% to approximately 1%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled *Aerosolisable Formulation*; GB 1817864.0, filed Nov. 1, 2018, titled *Aerosolisable Formulation*; GB 1817867.3, filed Nov. 1, 2018, titled Aerosolisable Formulation; GB 1817865.7, filed Nov. 1, 2018, titled *Aerosolisable Formulation*; GB 1817859.0, filed Nov. 1, 2018, titled *Aerosolisable Formulation*; GB 1817866.5, filed Nov. 1, 2018, titled *Aerosolisable Formulation*; GB 1817861.6, filed Nov. 1, 2018, titled Gel and Crystalline Powder; GB 1817862.4, filed Nov. 1, 2018, titled *Aerosolisable Formulation*; GB 1817868.1, filed Nov. 1, 2018, titled *Aerosolised Formulation*; and GB 1817860.8, filed Nov. 1, 2018, titled *Aerosolised Formulation*, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), melatonin, stimulants (e.g., caffeine, theine, and guarana), amino acids (e.g., taurine, theanine, phenylalanine, tyrosine, and tryptophan) and/or pharmaceutical, nutraceutical, nootropic, psychoactive, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibers, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: *Mentha arventis, Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens.*

As noted above, in various implementations, the liquid composition may include a flavorant or materials that alter the sensory or organoleptic character or nature of the aerosol of the smoking article. In some implementations, the flavorant may be pre-mixed with the liquid. In other implementations, the flavorant may be delivered separately downstream from the atomizer as a main or secondary flavor. Still other implementations may combine a pre-mixed flavorant with a downstream flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As used herein, the terms "flavor," "flavorant," "flavoring agents," etc. refer to materials which, where local regulations permit, may be used to create a desired taste, aroma, or other somatosensorial sensation in a product for adult consumers. They may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

In some implementations, the flavor comprises menthol, spearmint and/or peppermint. In some embodiments, the flavor comprises flavor components of cucumber, blueberry, citrus fruits and/or redberry. In some embodiments, the flavor comprises eugenol. In some embodiments, the flavor comprises flavor components extracted from tobacco. In some embodiments, the flavor comprises flavor components extracted from cannabis.

In some implementations, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to, eucolyptol or WS-3.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

Referring back to FIG. 2, in some implementations, such as the depicted implementation, the reservoir 144 is in fluid communication with at least a portion of an atomizing assembly 115 via one or more additional components. In some implementations, the reservoir 144 may comprise an independent container (e.g., formed of walls substantially impermeable to the liquid composition). In some implementations, the walls of the reservoir may be flexible and/or collapsible, while in other implementations the walls of the reservoir may be substantially rigid. In some implementations, the reservoir may be substantially sealed to prevent passage of the liquid composition therefrom except via any specific openings or conduits provided expressly for passage of the liquid composition, such as through one or more transport elements as otherwise described herein.

In the depicted implementation, an electrical connection 116 connects the atomizing assembly 115 to the base 140 of the cartridge 104, which, when assembled to the control unit 102, provides an electrical connection to the control component 106 and/or the power source 110. As noted, the atomizing assembly 115 is configured to be electrically connected to the power source 110 and/or the control component 106. In such a manner, the atomizing assembly 115 of the depicted implementation may be energized by the power source 110 and/or control component 106. In the depicted implementation, the atomizing assembly 115 is configured to vaporize (e.g., aerosolize, etc.) at least a portion of the liquid composition to generate an aerosol.

In the depicted implementation, the atomizing assembly 115 is fluidly coupled with at least a portion of the liquid composition in the reservoir 144 via a liquid delivery component 165. In the depicted implementation, the control unit housing 101 includes an air intake 118, which may comprise an opening in the housing proximate the coupler 124 allowing for passage of ambient air into the control unit housing 101 where it then passes through the cavity 125 of the coupler 124, and eventually into or around the atomizing assembly 115, where it may be mixed with the vaporized liquid composition to comprise the aerosol that is delivered to the user. It should be noted that in other implementations the air intake 118 is not limited being on or adjacent the control unit housing 101. For example, in some implementations, an air intake may be formed through the cartridge housing 103 (e.g., such that it does not enter the control unit 102) or some other portion of the aerosol delivery device 100. In the depicted implementation, a mouthpiece portion that includes an opening 128 may be present in the cartridge housing 103 (e.g., at a mouthend of the cartridge 104) to allow for egress of the formed aerosol from the cartridge 104, such as for delivery to a user drawing on the mouthend of the cartridge 104.

In various implementations, the cartridge 104 may also include at least one electronic component 150, which may include an integrated circuit, a memory component, a sensor, or the like, although such a component need not be included. In those implementations that include such a component, the electronic component 150 may be adapted to communicate with the control component 106 and/or with an external device by wired or wireless means. In various implementations, the electronic component 150 may be positioned anywhere within the cartridge 104 or its base 140. Some examples of electronic/control components that may be applicable to the present disclosure are described in U.S. Pat. App. Pub. No. 2019/0014819 to Sur, which is incorporated herein by reference in its entirety. Although in the depicted implementation the control component 106 and the flow sensor 108 are illustrated separately, it should be noted that in some implementations the control component and the flow sensor may be combined as an electronic circuit board with the air flow sensor attached directly thereto. In some embodiments, the air flow sensor may comprise its own circuit board or other base element to which it can be attached. In some embodiments, a flexible circuit board may be utilized. A flexible circuit board may be configured into a variety of shapes, include substantially tubular shapes. Configurations of a printed circuit board and a pressure sensor, for example, are described in U.S. Pat. App. Pub. No. 2015/0245658 to Worm et al., the disclosure of which is incorporated herein by reference. Additional types of sensing or detection mechanisms, structures, and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, when a user draws on the article 100, airflow may be detected by the sensor 108, and the atomizing assembly 115 may be activated, which may vaporize the liquid composition. As noted above, in some implementations drawing upon the mouthend of the article 100 causes ambient air to enter the air intake 118 and pass through the cavity 125 in the coupler 124 and the base 140. In the cartridge 104, the drawn air combines with the formed vapor to form the aerosol. The aerosol is whisked, aspirated, or otherwise drawn away from the atomizing assembly 115 and out of the mouth opening 128 in the mouthend of the article 100. As noted, in other implementations, in the absence of an airflow sensor, the atomizing assembly 115 may be activated manually, such as by a push button (not shown). Additionally, in some implementations, the air intake may occur through the cartridge or between the cartridge and the control unit. It should be noted that in some implementations, there may be one or more components between the atomizing assembly and the opening in the mouthend of the article. For example, in some implementations there may be a heating component located downstream from the atomizing assembly. In various implementations, the heating component may comprise any device configured to elevate the temperature of the generated aerosol, including, for example, one or more coil heating components, ceramic heating components, etc.

In some implementations, one or more input elements may be included with the aerosol delivery device (and may replace or supplement an airflow sensor, pressure sensor, or manual push button). In various implementations, an input element may be included to allow a user to control functions of the device and/or for output of information to a user. Any component or combination of components may be utilized as an input for controlling the function of the device. For example, one or more pushbuttons may be used as described in U.S. Pat. App. Pub. No. 2015/0245658 to Worm et al., which is incorporated herein by reference in its entirety. Likewise, a touchscreen may be used as described in U.S. Pat. App. Pub. No. 2016/0262454, to Sears et al., which is incorporated herein by reference in its entirety. As a further example, components adapted for gesture recognition based on specified movements of the aerosol delivery device may be used as an input. See U.S. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

In some implementations, an input element may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such implementations, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Yet other features, controls or components that may be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, the atomizing assembly may comprise a variety of different components or devices configured to generate an aerosol from the liquid composition. For example, in some implementations the atomizing assembly may comprise a jet nebulizer assembly, which may be configured to utilize compressed air to generate an aerosol. In other implementations, the atomizing assembly may comprise an ultrasonic assembly, which may be configured to utilize the formation of ultrasonic waves within the liquid composition to generate an aerosol. In other implementations, the atomizing assembly may comprise a vibrating assembly, such as, for example, a vibrating mesh assembly, which may comprise a piezoelectric material (e.g., a piezoelectric ceramic material) affixed to and substantially surrounding a mesh plate, (e.g., a perforated plate such as a micro-perforated mesh plate) that is vibrated within the liquid composition or proximate the surface of the liquid composition to generate an aerosol. In still other implementations, the atomizing assembly may comprise a surface acoustic wave (SAW) or Raleigh wave assembly, which may utilize surface wave characteristics to generate an aerosol at the surface of the liquid composition. It should be noted that for purpose of this application, an ultrasonic assembly may be any assembly configured to create ultrasonic waves within the liquid composition. In some implementations, for example, a vibrating mesh assembly may also operate as an ultrasonic assembly.

Figure 3:
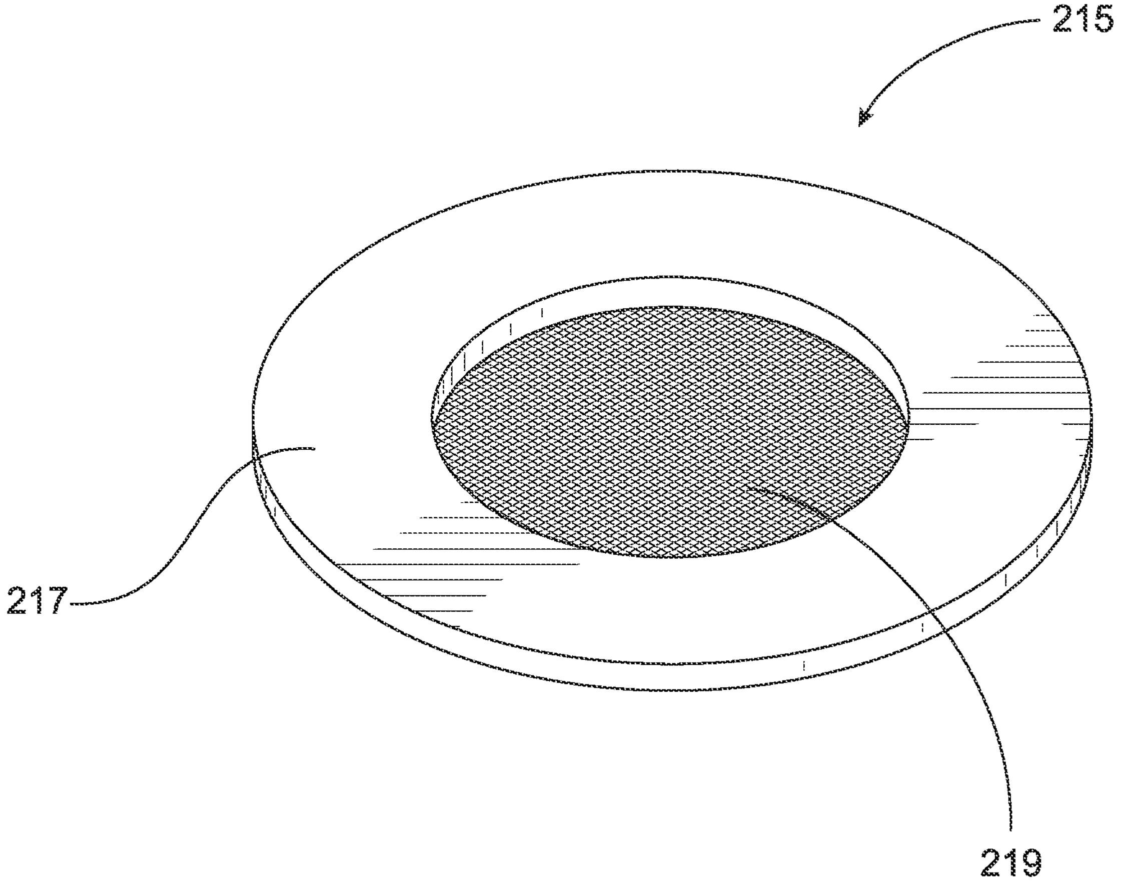
FIG. 3 a perspective view of an atomizing assembly, according to an example implementation of the present disclosure.

One example of an atomizing assembly comprising a vibrating assembly is shown in FIG. 3. In particular, FIG. 3 illustrates an atomizing assembly 215 that comprises a vibrating component 217 and a mesh plate 219. Although other configuration as possible, in the depicted implementation the vibrating component 217 comprises a piezoelectric component. In some implementations, additional components may be included. For example, in some implementations a supporting component may be included that is located on the side of the mesh plate opposite the vibrating component (e.g., such that the mesh plate is sandwiched between the supporting component and the vibrating component). Although other configurations are possible, in some implementations, the supporting component may comprise a supporting ring. In various implementations, the supporting component may be made of any suitable material, including, but not limited to, polymeric, metal, and/or ceramic materials. In such a manner, in some implementations the supporting component may increase the longevity of the mesh plate. In some implementations, the supporting component may be replaceable, while in other implementations the supporting component may be affixed to the mesh plate and/or the vibrating component. In some implementations, an auxiliary component may be used that is located between mesh plate and the vibrating component. Although other configurations are possible, in some implementations, the auxiliary component may comprise an auxiliary ring. In various implementations, the auxiliary component may be made of any suitable material, including, but not limited to, polymeric, metal, and/or ceramic materials. In such a manner, the auxiliary component may facilitate the interfacial contact of the components. In some implementations, the auxiliary component may be replaceable, while in other implementations the auxiliary component may be affixed to the mesh plate and/or the vibrating component.

In some implementations, the vibrating component and the mesh plate may be permanently affixed to each other such as, for example, by affixing the components together via an adhesive, such as, for example, an epoxy or other glue, or by ultrasonic welding, mechanical fasteners, etc., while in other implementations, the vibrating component and the mesh plate may not be permanently affixed to each other. Rather, they may be separable and held or forced into contact with each other. In various implementations, the mesh plate may have a variety of different configurations. For example, in some implementations the mesh plate may have a substantially flat profile. In other implementations, the mesh plate may have a substantially domed shape, which may be concave or convex with respect to the reservoir and/or the liquid composition. In other implementations, the mesh plate may include a substantially flat portion and a domed portion. In various implementations, the mesh plate may be made of a variety of different materials. In some implementations, the mesh plate may be made of a metal material, such as, but not limited to, stainless steel, palladium-nickel, or titanium. In other implementations, the mesh plate may be made of a polymeric material, such as, for example, a polyimide polymer. In still other implementations, the mesh plate may be made of a combination of materials.

Figure 4A:
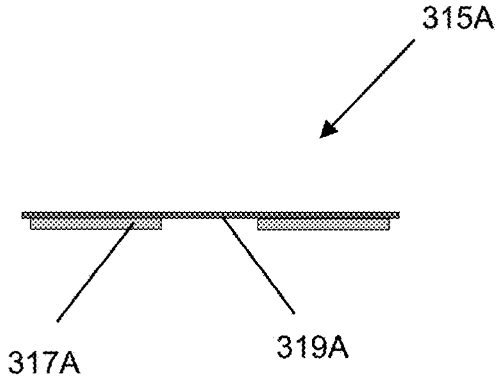
FIG. 4A illustrates a side schematic view of a portion of an atomizing assembly, according to an example implementation of the present disclosure.
Figure 4B:
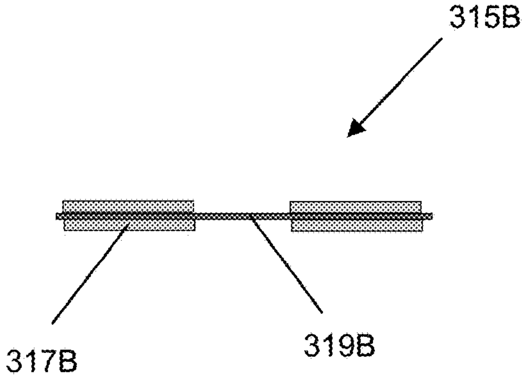
FIG. 4B illustrates a side schematic view of a portion of an atomizing assembly, according to an example implementation of the present disclosure.
Figure 4C:
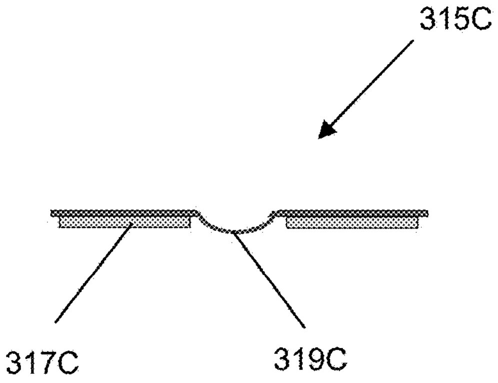
FIG. 4C illustrates a side schematic view of a portion of an atomizing assembly, according to an example implementation of the present disclosure.
Figure 4D:
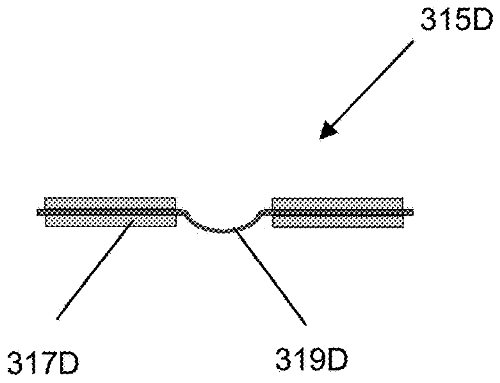
FIG. 4D illustrates a side schematic view of a portion of an atomizing assembly, according to an example implementation of the present disclosure.
Figure 4E:
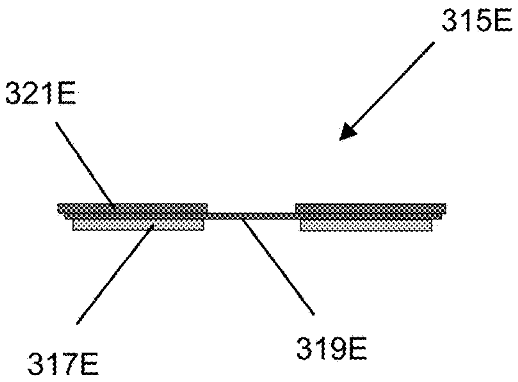
FIG. 4E illustrates a side schematic view of a portion of an atomizing assembly, according to an example implementation of the present disclosure.
Figure 4F:
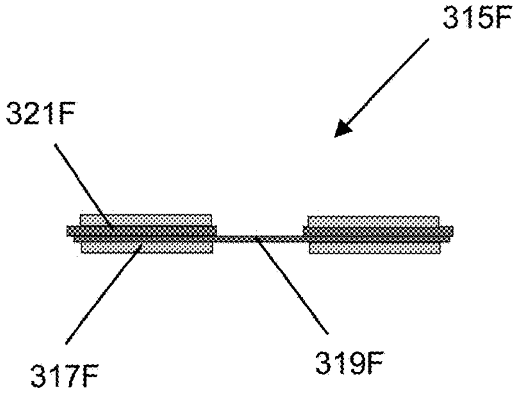
FIG. 4F illustrates a side schematic view of a portion of an atomizing assembly, according to an example implementation of the present disclosure.

As noted, in various implementations the structure of the atomization assembly may vary. For example, FIGS. 4A-4F illustrate example implementations of various atomization assemblies. In some implementations, the atomizing assembly of the implementation depicted in FIG. 1 may have one of these configurations. In particular, FIG. 4A illustrates an atomizing assembly 315A comprising a piezoelectric component 317A affixed to and substantially surrounding a mesh plate 319A. FIG. 4B illustrates an atomizing assembly 315B comprising a mesh plate 319B sandwiched between two portions of a piezoelectric component 317B. FIG. 4C illustrates an atomizing assembly 315C comprising a piezoelectric component 317C affixed to and substantially surrounding a mesh plate 319C, wherein at least a portion of the mesh plate 319C is curved. FIG. 4D illustrates an atomizing assembly 315D comprising a mesh plate 319D sandwiched between two portions of a piezoelectric component 317D, wherein at least a portion of the mesh plate 319D is curved. FIG. 4E illustrates an atomizing assembly 315E comprising a piezoelectric component 317E affixed to and substantially surrounding one side of a mesh plate 319E, wherein the other side of the mesh plate 319E includes a metal ring 321E substantially surrounding and affixed thereto. FIG. 4F illustrates an atomizing assembly 315F comprising a mesh plate 319F one side of which includes a metal component 321F substantially surrounding and affixed thereto, the mesh plate 319F and metal component 321F sandwiched between two portions of a piezoelectric component 317F. It should be noted that in other implementations one or both of the atomization assemblies of the present disclosure need not be limited to these configurations.

Referring back to FIG. 3, the mesh plate 219 of the depicted implementation includes a plurality of perforations. In some implementations, the perforations may be defined by circular openings in the surfaces of the plate. In other implementations, the perforations may be defined by non-circular openings in the surfaces of the plate, such as, for example, oval, rectangular, triangular, or regular or irregular polygon openings. In various implementations, the perforations may be created using a variety of different methods, including, but not limited to, via a laser (e.g., a femtosecond laser) or via electroplating (e.g., lithography or focused ion beams) or via use of high or low energy focused ion or electron beams. In various implementations, the shapes defined through the plate by the perforations may vary. For example, in some implementations the shapes defined through the plate by the perforations may be substantially cylindrical. In other implementations, the shapes defined through the plate by the perforations may be substantially conical (e.g., having a truncated conical shape defining smaller openings on one surface of the plate and larger openings on the opposite surface of the plate). In other implementations, the shapes defined through the plate by the perforations may be tetragonal or pyramidal. It is believed that in some implementations, substantially conical perforations may increase the performance of the mesh in atomizing the liquid composition. Although any orientation of the mesh plate may be used, in some implementations with perforations defining substantially conical shapes through the plate, the larger openings may be located proximate the surface of the liquid composition and the smaller openings may define an aerosol outlet area. In some implementations with perforations having a substantially conical shapes, the smaller openings may have a size in the inclusive range of approximately 1 micron up to approximately 10 microns, with an average size of approximately 2 microns to approximately 5 microns. In other implementations, the smaller openings may have a size in the inclusive range of approximately several hundred nanometers up to approximately 4 microns, with an average size of approximately 2 microns to approximately 3.1 microns. In other implementations, the smaller end may have a size in the inclusive range of approximately several hundred nanometers to approximately 2 microns, with an average size of approximately 1 micron. In some implementations, the larger openings may have a size in the inclusive range of approximately 10 microns to approximately 60 microns, with an average size of approximately 20 microns to approximately 30 microns. In other implementations, the larger openings may have a size in the inclusive range of approximately 5 microns to approximately 20 microns, with an average size of approximately 10 microns. In some implementations, the size of the perforations may be substantially uniform throughout the perforated portion of the plate; however, in other implementations, the size of the perforations may vary. In such a manner, the formed aerosol may have different size aerosol droplets. For example, in some implementations the perforations may be larger in one portion of the plate and smaller in another portion of the plate. Such portions may include, for example, the center of the plate and a periphery of the plate, or alternating rings that extend radially from the center of the plate.

In various implementations, the mesh plate may have any number of perforations. In some implementations, for example, a number of perforations in the mesh plate may be in the inclusive range of approximately 200 to approximately 6,000, with an average number of perforations of approximately 1,100 to approximately 2,500. In other implementations, a number of perforations in the mesh plate may be in the inclusive range of approximately 400 to approximately 1,000. In various implementations, the thickness of the vibrating component and the thickness of the mesh plate may vary. For example, in some implementations the thickness of the mesh plate may be in the range of a few microns to a few millimeters. In various implementations, the overall diameter of a mesh plate may vary. For example, in some implementations the overall diameter of the mesh plate may be in the inclusive range of approximately a few millimeters to approximately 30 millimeters. In some implementations, the outer diameter of the vibrating component may be larger than the overall diameter of the mesh plate. In other implementations, the outer diameter of the vibrating component may be substantially the same size as the overall diameter of the mesh plate. In still other implementations, the outer diameter of the vibrating component may be smaller than the overall diameter of the mesh plate. In various implementations, the diameter of the perforation area may be smaller than the overall diameter of the mesh plate. For example, in some implementations the diameter of the perforated area may be in the inclusive range of approximately 1 millimeter to approximately 20 millimeters, with an average of approximately 4 millimeters to approximately 12 millimeters. In some implementations, the inner diameter of the vibrating component may be larger than the diameter of the perforated area of the mesh plate. In other implementations, the inner diameter of the vibrating component may be substantially the same as, or smaller than, the diameter of the perforated area of the mesh plate. In some implementations, the thickness of the vibrating component may be in the inclusive range of a few hundred microns to tens of millimeters. For example, in some implementations the thickness of the vibrating component may be smaller than 1 millimeter.

As noted above, in some implementations the vibrating component may comprise a piezoelectric component. For example, in various implementations the vibrating component may comprise a piezoelectric ring, which, in some implementations may be made of a piezoceramic material. It should be noted that while the depicted implementation describes a piezoelectric component in the form of a piezoelectric ring, in other implementations the piezoelectric component need not be limited to a ring-shaped object. For example, in some implementations the piezoelectric component may have rectangular, oval, hexagonal, triangular, and regular or irregular polygon shapes. In general, piezoceramic materials possess piezoelectric properties (e.g., ferroelectric properties), wherein they are configured to change shape to a small extent (e.g., 1-2 microns in our application) when exposed to an electrical stimulus. This occurs due to a shift in the crystal structure of the piezoceramic materials (e.g., from orthorhombic to cubic, or hexagonal to cubic, etc.). With respect to a piezoceramic ring, such a change in shape results in an internal strain and therefore shrinkage of the disc that results in bending of the disk due to its rigid structure. Because the ring is affixed to the mesh plate, the bending of the ring is transferred to the mesh material. When the electric current is disconnected from the piezoelectric ring, the ring and mesh plate return to their original shape and position. As such, a continuous change of the shape and position will result in an oscillating motion that can be used as a vibration source. In various implementations, the frequency of the piezoelectric ring may be in the range of a few Hz to several MHz. For example, in some implementations the frequency of the piezoelectric ring in in the inclusive range of approximately 50 KHz to approximately 150 KHz, with an average, in one implementation of approximately 110 KHz, in another implementation of approximately 113 KHz, in another implementation of approximately 117 KHz, in another implementation, of approximately 130 KHz, in another implementation, of approximately 150 KHz, in another implementation, of approximately 170 KHz, and in another implementation, of approximately 250 KHz. In other implementations, the frequency of the piezoelectric ring is in the inclusive range of approximately 1 MHz to approximately 5 MHz, with an average of approximately 3 MHz to approximately 3.5 MHz.

In various implementations, a variety of different piezoelectric materials are possible, including natural or synthetic materials. Some non-limiting examples of natural piezoelectric materials include, for example, quartz, berlinite ($AlPO_4$), sucrose, rochelle salt, topaz, tourmaline-group minerals, lead titanate ($PbTiO_3$), and collagen. Some non-limiting examples of synthetic materials include, for example, a ($La_3Ga_5SiO_{14}$), gallium phosphate, gallium orthophosphate ($GaPO_4$), lithium niobate ($LiNbO_3$), lithium tantalate ($LiTaO_3$), AlN, ZnO, barium titanate ($BaTiO_3$), lead zirconate titanate ($Pb[Zr_xTi_{1-x}]O_3$) (a.k.a. PZT), potassium niobate ($KNbO_3$), sodium tungstate ($Na_2WO_3$), $Ba_2NaNb_5O_5$, $Pb_2KNb_5O_{15}$, zinc oxide (ZnO), sodium potassium niobate ($(K,Na)NbO_3$) (a.k.a. NKN), bismuth ferrite ($BiFeO_3$), sodium niobate $NaNbO_3$, barium titanate ($BaTiO_3$), bismuth titanate $Bi_4Ti_3O_{12}$, sodium titanate, and sodium bismuth titanate $NaBi(TiO_3)_2$. In other implementations, polymers exhibiting piezoelectric characteristics may be used, including, but not limited to, polyvinylidene fluoride (PVDF).

In various implementations, a mesh plate of an atomizing assembly may be in contact with at least a portion of a liquid composition, and/or may be proximate at least a portion of a liquid composition, and/or may receive at least a portion of a liquid composition, such as via a liquid delivery component. In such a manner, the resulting vibration of the plate generates an aerosol from the contacted liquid composition. In particular, in some implementations, the liquid composition is driven through the plurality of micro perforations resulting in the generation of a plurality of aerosol particles. Likewise, in other implementations, such as, for example, implementations in which the mesh plate is immersed in the liquid composition, vibration of the plate creates ultrasonic waves within the liquid composition that result in the formation of an aerosol at the surface of the liquid composition. As will be described in more detail below, in other implementations the liquid composition may be applied and/or transferred to the atomizing assembly to create the aerosol. In various implementations, the mesh plate may be made of a variety of materials, including for example, one or more metal materials, such as titanium, stainless steel, palladium, nickel, etc., or a polymer material, such as polyimides materials, etc.

Referring back to FIG. 1, in the depicted implementation the atomizing assembly 115 may be controlled via the control component 106 and/or the power source 108. In such a manner, control of the atomizing assembly 115 may be automatic or on-demand. In some implementations, automatic activation of the atomizing assembly may be triggered, for example, by a draw on the device by a user. In some implementations, on-demand activation of the atomizing assembly may be activated using an input element, such as, for example, a pressure activated device (e.g., one or more push-buttons). In the depicted implementation, a portion of the liquid composition 145 is configured to be delivered to the atomizing assembly 115 by the liquid delivery component 165.

Figure 5:
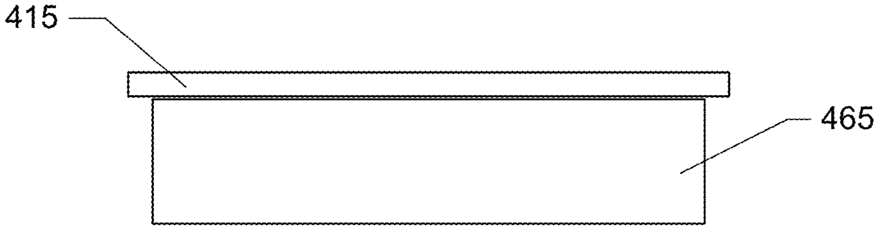
FIG. 5 illustrates a side schematic view of a liquid delivery and atomizing assembly, according to an example implementation of the present disclosure.

In various implementations, the structure and/or the manner in which the liquid delivery component delivers liquid composition to the atomizing assembly may vary. For example, FIG. 5 illustrates a side schematic view of a liquid delivery component 465 and atomizing assembly 415, according to one example implementation of the present disclosure, wherein the liquid delivery component 465 is configured to deliver at least portion of the liquid composition to the atomizing assembly 415. In the depicted implementation, the liquid delivery component 465 comprises a piezoelectric micropump. In some implementations, the piezoelectric micropump may comprise a piezoelectric diaphragm that is configured to deflect or oscillate between two positions that are configured to move fluid through the pump, such as, for example, from the liquid reservoir to the atomizing assembly. In some implementations, the piezoelectric diaphragm may comprise a substantially circular diaphragm, and the piezoelectric diaphragm may be made of a piezoelectric ceramic material. As noted generally above, piezoceramic materials possess piezoelectric properties (e.g., ferroelectric properties), wherein they are configured to change shape to a small extent (e.g., 1-2 microns in our application) when exposed to an electrical stimulus. This occurs due to a shift in the crystal structure of the piezoceramic materials (e.g., from orthorhombic to cubic, or hexagonal to cubic, etc.). In some implementations, one or more valves may assist in pumping the fluid.

Figure 6A:
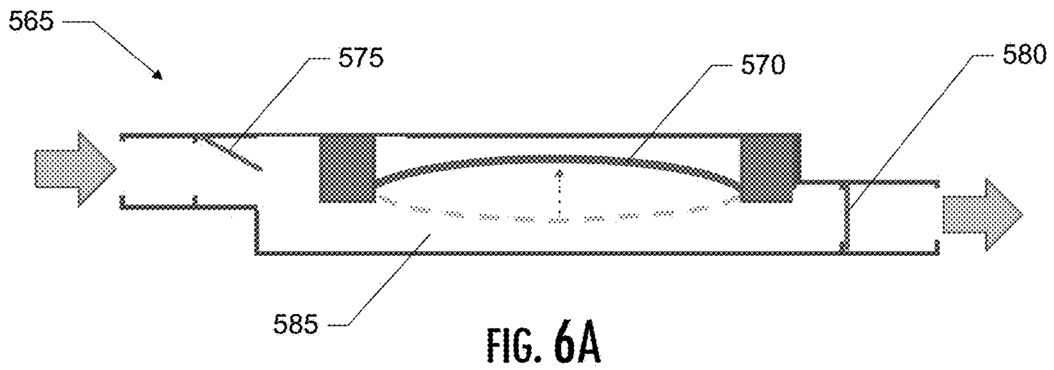
FIG. 6A illustrates a side schematic view of a liquid delivery component, according to an example implementation of the present disclosure.
Figure 6B:
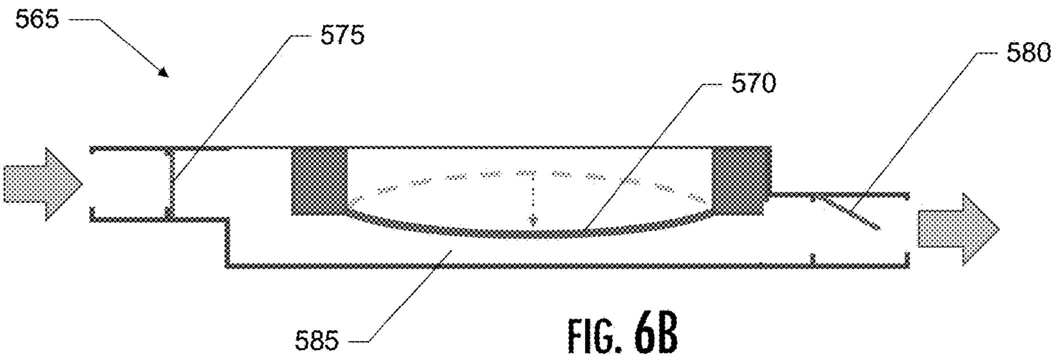
FIG. 6B illustrates a side schematic view of a liquid delivery component, according to an example implementation of the present disclosure.

One example implementation of a piezoelectric micropump is shown in FIGS. 6A and 6B. In particular, FIGS. 6A and 6B illustrate side schematic views of a liquid delivery component 565, according to another example implementation of the present disclosure. In the depicted implementation, the liquid delivery component 565 includes a piezoelectric diaphragm 570 configured to deflect (e.g., upward and downward as oriented in the drawing) so as the move fluid through the liquid delivery component 565. The liquid delivery component 565 of the depicted implementation further includes a pair of one-way valves, an inlet valve 575 and an outlet valve 580, and a fluid chamber 585. As illustrated in FIG. 6A, when the piezoelectric diaphragm 570 of the depicted implementation moves upward, fluid is drawn through the inlet valve 575 and into the fluid chamber 585. As illustrated in FIG. 6B, when the piezoelectric diaphragm 570 of the depicted implementation moves downward, fluid is pushed out of the fluid chamber 585 and through the outlet valve 580. In such a manner, the liquid delivery component 565 of the depicted implementation may provide controlled delivery of a portion of the liquid composition to an atomizing device.

In some implementations, the piezoelectric micropump may operate under control of the same controller as used for other functions of the aerosol delivery device. In other implementations, the piezoelectric micropump may operate under control of an independent controller. In some implementations, delivery of the liquid composition to the atomizing assembly may occur in response to a draw by a user on the aerosol delivery device, such as, for example, in response to a signal from a pressure sensor of the aerosol delivery device. In some implementations, the piezoelectric micropump may be gravity fed and the outlet may deliver liquid directly to the atomizing assembly. In other embodiments, a liquid transport element may facilitate delivery of liquid to the piezoelectric micropump and/or to the atomizing assembly. In some implementations, the liquid transport element may be made of fibrous materials (e.g., organic cotton, cellulose acetate, regenerated cellulose fabrics, glass fibers), polymers, silk, particles, porous ceramics (e.g., alumina, silica, zirconia, SiC, SiN, AlN, etc.), porous metals, porous carbon, graphite, porous glass, sintered glass beads, sintered ceramic beads, capillary tubes, porous polymers, or the like. In some implementations, the liquid transport element may be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. In some embodiments, the liquid transport element may be a substantially solid non-porous material, such as a polymer or dense ceramic or metals, or superabsorbent polymers, configured to channel liquid through apertures or slots while not necessarily relying upon wicking through capillary action. Such a solid body may be used in combination with a porous absorptive pad. The absorptive pad may be formed of silica-based fibers, organic cotton, rayon fibers, cellulose acetate, regenerated cellulose fabrics, highly porous ceramic or metal mesh, etc. In some implementations, the liquid transport element may comprise a mutli-lobal ceramic or other material (such as any one or combination of the materials described above) that may be formed through an extrusion technique.

Some implementations may include a piezoelectric micropump and a vibrating mesh that includes a piezoelectric material. In some implementations, vibration of the piezoelectric micropump and the vibrating mesh may be synchronized. For example, in some implementations upon a draw from a user (e.g., puff activation) the liquid composition may first be delivered to the vibrating mesh by the piezoelectric micropump and subsequently atomized by the vibrating mesh. It should be noted, however, that in some implementations the vibration frequencies of the piezoelectric micropump and the vibrating mesh need not be synchronized in order to have the liquid delivery rate synchronized with the atomization rate. For example, in some implementations, any one or any combination of parameters may have the same effect. Such parameters may include, but need not be limited to, a size of the micropump discharge channel, a micropump maximum head, a liquid viscosity/density of the liquid composition, inlet and/or discharge channel dimensions (e.g., length and/or diameter), etc. In some implementations, the vibration frequency of the piezoelectric micropump may be different than the vibration frequency of the vibrating mesh. In other implementations, the vibration frequency of the piezoelectric micropump may substantially match (e.g., be substantially the same as) the vibration frequency of the vibrating mesh.

Figure 7:
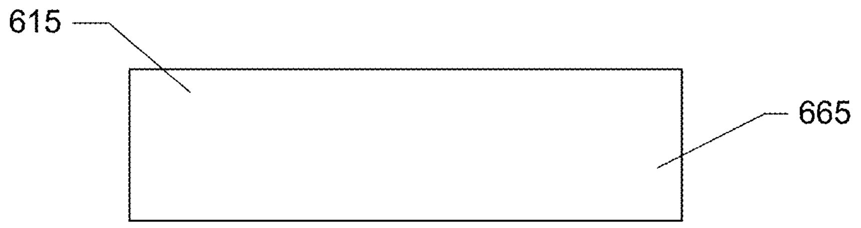
FIG. 7 illustrates a side schematic view of a liquid delivery component and atomizing assembly, according to an example implementation of the present disclosure.

In some implementations, the piezoelectric micropump and the vibrating mesh may be integrated together using a common element. For example, in some implementations the vibrating mesh may include a piezoelectric material that is integrated with the piezoelectric micropump. In some implementations, the piezoelectric material of the vibrating mesh and the piezoelectric micropump may have a common piezoelectric element. FIG. 7 illustrates one example of such an implementation. In general, FIG. 7 illustrates a side schematic view of a liquid delivery and atomizing assembly, according to another example implementation of the present disclosure. In particular, FIG. 7 illustrates an atomizing assembly 615 and a liquid delivery component 665. In the depicted implementation, the atomizing assembly 615 comprises a vibrating mesh that includes a piezoelectric material, and the liquid delivery component 665 comprises a piezoelectric micropump. Reference is made to the descriptions above relating to possible vibrating mesh and micropump implementations. In the depicted implementation, the piezoelectric material of the atomizing assembly 615 and the piezoelectric material of the piezoelectric micropump comprise the same piezoelectric material. As such, the vibration frequency of the atomizing assembly 615 and the piezoelectric micropump of the depicted implementation may be substantially the same.

Figure 8:
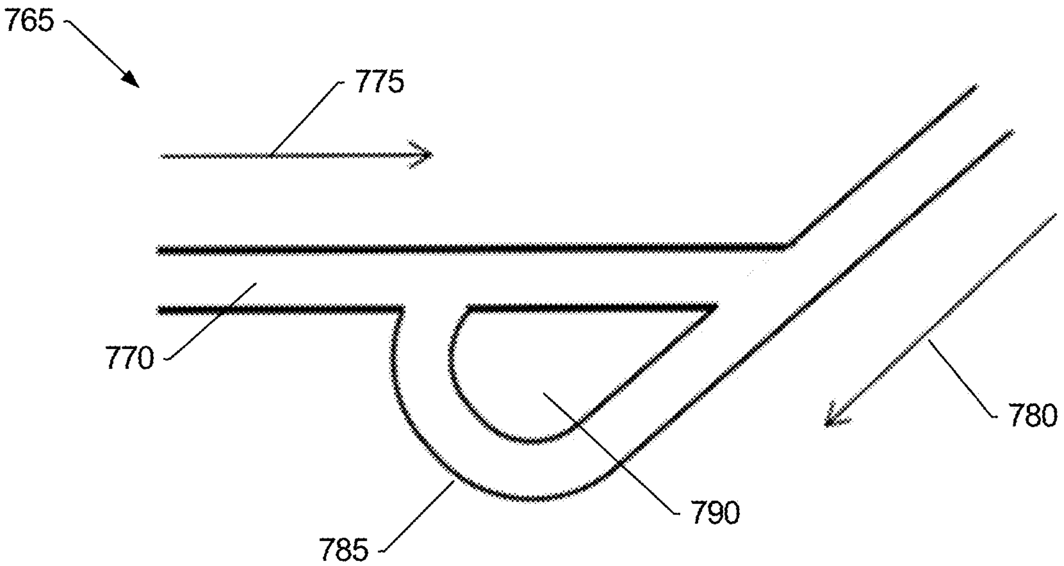
FIG. 8 illustrates a side schematic view of a liquid delivery component, according to an example implementation of the present disclosure.

FIG. 8 illustrates a side schematic view of a liquid delivery component, according to another example implementation of the present disclosure. In particular, FIG. 8 illustrates a liquid delivery component 765 in the form of a Tesla valve. It should be noted that although the depicted implementation comprises a single Tesla valve segment, in other implementations the liquid delivery component may comprise a series (e.g., two or more) of Tesla valve segments. In the depicted implementation, the Tesla valve segment includes a main channel 770 configured to allow the flow of liquid composition in only one direction, for example, from the reservoir (or other liquid compositions source, such as a liquid transport element), to the atomizing assembly. As shown in FIG. 8, the liquid composition may follow the left to right flow direction 775 (as oriented in the drawing) from the reservoir to the atomizing assembly. The valve resists flow, however, in the opposite direction 780. This resistance is provided by the geometry of the valve, and in particular, the bucket(s) 785 and independent partition(s) 790 of the valve geometry. In the depicted implementation, the liquid delivery component 765 does not include any moving components. In other implementations, however, one or more moving parts may be used in conjunction with the liquid delivery component, such as to help deliver the liquid composition from the reservoir to the liquid delivery component or away from the liquid delivery component to the atomizing assembly.

Figure 9:
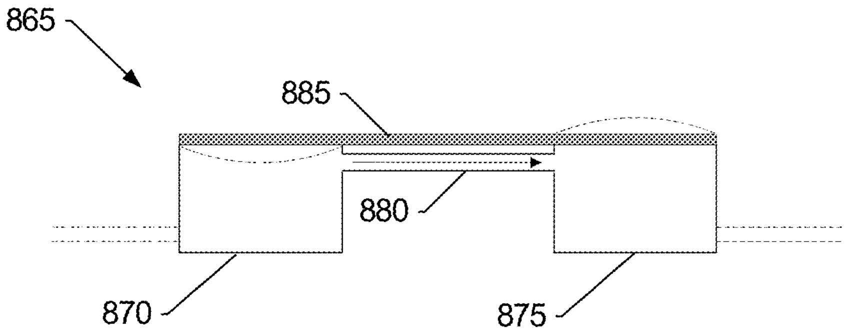
FIG. 9 illustrates a side schematic view of a liquid delivery component, according to an example implementation of the present disclosure.

FIG. 9 illustrates a side schematic view of a liquid delivery component, according to another example implementation of the present disclosure. In particular, FIG. 9 illustrates a liquid delivery component 865 in the form of an electroosmotically driven micropump. In the depicted implementation, the liquid delivery component 865 comprises a supply chamber 870, an expansion chamber 875, and at least one microchannel 880 extending between the two. The liquid delivery component 865 also includes a membrane 885 (e.g., a polymer membrane), which is connected to a power source (e.g., via electrodes). Voltage applied to the membrane causes one portion of the membrane to deflect downward (as oriented in the drawing) and another portion of the membrane to deflect upward. In particular, when voltage is applied to the membrane 885 of the depicted implementation, the portion of the membrane 885 over the supply chamber 870 deflects downward and the portion of the membrane 885 over the expansion chamber 875 deflects upward. Such deflection causes liquid composition to be pumped from the supply chamber 870 to the expansion chamber 875. In some implementations, the level of deflection is increased with increased voltage applied to the membrane. In the depicted implementation, the liquid composition may enter the supply chamber 870 from the reservoir, and the expansion chamber 875 may deliver the liquid composition to the atomizing assembly. In some implementations, the reservoir may comprise the supply chamber. In some implementations, one or more liquid transport elements may transfer the liquid composition from the expansion chamber to the atomizing assembly. In some implementations, the liquid delivery component of the depicted implementation may be used in conjunction with one or more other implementations of the liquid delivery component.

Figure 10B:
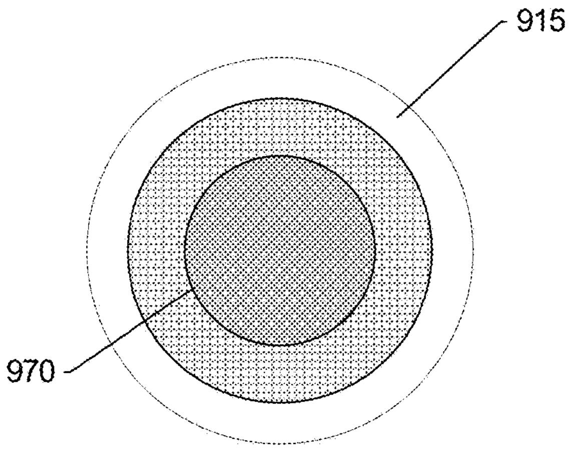
FIG. 10B illustrates a top schematic view of a liquid delivery component and atomizing assembly, according to an example implementation of the present disclosure.
Figure 10A:
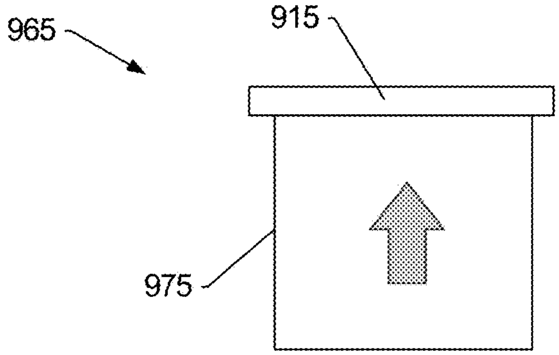
FIG. 10A illustrates a side schematic view of a liquid delivery component and atomizing assembly, according to an example implementation of the present disclosure.

FIG. 10A illustrates a side schematic view of a liquid delivery component and FIG. 10B illustrates a top schematic view of the liquid delivery component, according to another example implementation of the present disclosure. In particular, FIGS. 10A and 10B illustrate a liquid delivery component 965 in the form of a biomimetic micropump. This micropump is modeled on the water transfer mechanism exhibited by plants, sometimes referred to as transpiration. During transpiration, water is draw upward into a plant's roots and transferred through the plant's vascular structures (e.g., the plant xylem) as moisture is evaporated from distal portions of the plant, such as the plant's leaves or flowers. This transfer is driven by the lower pressure caused by the release of the water vapor thus promoting the transfer of liquid to a lower pressure gradient. In the depicted implementation, this behavior is modeled using geometric structures based on xylem model components (e.g., ceramics or other controllable materials, etc.) and leaf model components (e.g., microperforated structures). In the depicted implementation, the liquid delivery component 965 comprises a leaf model component 970 and a xylem model component 975. In the depicted implementation, the leaf model component 970 comprises a plate having a plurality of openings (e.g., a mesh plate) configured to allow evaporation of a portion of the liquid composition, which allows the transfer of liquid through the xylem model component 975. In some implementations, the openings may be defined by circular openings in the surfaces of the leaf model component. In other implementations, the openings may be defined by slits in the leaf model component. In still other implementations, the openings may be defined by other non-circular openings in the surfaces of the plate, such as, for example, oval, rectangular, triangular, or regular or irregular polygon openings. In various implementations, the openings may be created using a variety of different methods, including, but not limited to, via a laser (e.g., a femtosecond laser) or via electroplating (e.g., lithography or focused ion beams) or via use of high or low energy focused ion or electron beams. In various implementations, the shapes defined through the leaf model component by the perforations may vary.

In some implementations, the liquid composition may enter the xylem model component from the reservoir and deliver a portion of the liquid composition to the atomizing assembly. Although in other implementations they may be separate components, in the depicted implementation the leaf model component 970 comprises a portion of the atomizing assembly 915. In particular, the leaf model component 970 of the depicted implementation is integrated with a vibrating component of the atomizing assembly 915. In such a manner, in the depicted implementation a portion of the liquid composition may be delivered through the xylem model component 975 to the leaf model component 970 where it is evaporated, and another portion of the liquid composition may be delivered to the vibrating component of the atomizing assembly 915 where it is vaporized into an aerosol for delivery to a user. Although other configurations are possible, in the depicted implementation the leaf model component 970 comprises a central portion of the atomizing assembly 915 (e.g., a central area of a mesh plate) and the portion of the liquid composition that is vaporized to generate an aerosol comprises a peripheral portion of the atomizing assembly 915 (e.g., a peripheral area of the mesh plate). In some implementations, the xylem model component may comprise the supply chamber. In some implementations, one or more liquid transport elements may transfer the liquid composition from the reservoir to the xylem model component and/or from the xylem model component to the atomizing assembly.

It should be noted that in some implementations, the liquid delivery component of any depicted or described implementation may be used in conjunction with one or more other depicted or described implementations of the liquid delivery component.

As noted above, in some implementations a liquid delivery component of the present disclosure may be gravity fed and the outlet may deliver liquid to the atomizing assembly, either directly or indirectly. In other implementations, one or more liquid transport elements may be used in conjunction with a liquid delivery component. For example, in some implementation a liquid transport element may be made of fibrous materials (e.g., organic cotton, cellulose acetate, regenerated cellulose fabrics, glass fibers), polymers, silk, particles, porous ceramics (e.g., alumina, silica, zirconia, SiC, SiN, AlN, etc.), porous metals, porous carbon, graphite, porous glass, sintered glass beads, sintered ceramic beads, capillary tubes, porous polymers, or the like. In some implementations, the liquid transport element may be any material that contains an open pore network (i.e., a plurality of pores that are interconnected so that fluid may flow from one pore to another in a plurality of direction through the element). The pores can be nanopores, micropores, macropores or combinations thereof. As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. In some embodiments, the liquid transport element may be a substantially solid non-porous material, such as a polymer or dense ceramic or metals, or superabsorbent polymers, configured to channel liquid through apertures or slots while not necessarily relying upon wicking through capillary action. Such a solid body may be used in combination with a porous absorptive pad. The absorptive pad may be formed of silica-based fibers, organic cotton, rayon fibers, cellulose acetate, regenerated cellulose fabrics, highly porous ceramic or metal mesh, etc. In some implementations, the liquid transport element may comprise a mutlilobal ceramic or other material (such as any one or combination of the materials described above) that may be formed through an extrusion technique.

Some representative types of reservoirs or other components for supporting the liquid composition are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In various implementations, woven and/or non-woven aramid fibers may be utilized in a liquid transport element. In some implementations, the liquid transport element may be formed partially or completely from a porous monolith, such as a porous ceramic, a porous glass, or the like. Example monolithic materials that may be suitable for use according to embodiments of the present disclosure are described, for example, in U.S. Pat. App. Pub. No. 2017/0188626 to Davis et al., and U.S. Pat. App. Pub. No. 2014/0123989 to LaMothe, the disclosures of which are incorporated herein by reference in their entireties. In some implementations, the porous monolith may form a substantially solid wick.

In some implementations, in addition to aerosolization of the liquid composition via at least one atomizing assembly, such as, for example, via a vibrating assembly comprising a piezoelectric component, aerosolization may occur via one or more aerosolizing heating arrangements, which in some implementations may heat the piezoelectric component of the atomizing assembly in order to further or alternatively aerosolize a portion of the liquid composition. In various implementations, such an aerosolization heating arrangement may include, but need not be limited to, an inductive heating arrangement, a resistive heating arrangement, and/or a microwave heating arrangement. In some implementations, the aerosolizing heating arrangement may comprise an aerosolizing inductive heating arrangement that includes an aerosolizing resonant transmitter and an aerosolizing resonant receiver (e.g., one or more aerosolizing susceptors). In some implementations, the aerosolizing resonant transmitter may be the same resonant transmitter or a different resonant transmitter as that used as the liquid delivery resonant transmitter. For example, in some implementations the resonant transmitters may comprise the same helical coil. In some implementations, the aerosolizing susceptor may be part of the atomizing assembly, such as, for example, the piezoelectric component. For instance, in various implementations at least a portion of the piezoelectric component may be coated with one or more materials (e.g., ferromagnetic and/or non-ferromagnetic materials) configured to generate heat using a resonant transmitter, such as an induction coil. For example, in some implementations at least a portion of the piezoelectric component may be coated with ferromagnetic materials including, but not limited to, cobalt, iron, nickel, zinc, manganese, and any combinations thereof. In other implementations, the piezoelectric component may be coated with metal materials such as, but not limited to, aluminum or stainless steel, as well as ceramic materials such as, but not limited to, silicon carbide, carbon materials, and any combinations of any of the materials described above. In still other implementations, the materials may comprise other conductive materials including metals such as copper, alloys of conductive materials, or other materials with one or more conductive materials imbedded therein. In such a manner, atomization assemblies of some implementations may generate aerosol using both vibration and thermal energy, simultaneously or individually. It should be noted that in some implementations, instead of a coating, one or more of the abovementioned materials may be loaded into the bulk piezoelectric component and/or in the form of macro/micro/nano-particles.

Although in some implementations of the present disclosure a cartridge and a control unit may be provided together as a complete aerosol delivery device generally, these components may be provided separately. For example, the present disclosure also encompasses a disposable unit for use with a reusable unit. In specific implementations, such a disposable unit (which may be a cartridge as illustrated in the appended figures) can be configured to engage a reusable unit (which may be a control unit as illustrated in the appended figures). In still other configurations, a cartridge may comprise a reusable unit and a control unit may comprise a disposable unit.

Although some figures described herein illustrate a cartridge and a control unit in a working relationship, it is understood that the cartridge and the control unit may exist as individual components. Accordingly, any discussion otherwise provided herein in relation to the components in combination also should be understood as applying to the control unit and the cartridge as individual and separate components.

In another aspect, the present disclosure may be directed to kits that provide a variety of components as described herein. For example, a kit may comprise a control unit with one or more cartridges. A kit may further comprise a control unit with one or more charging components. A kit may further comprise a control unit with one or more batteries. A kit may further comprise a control unit with one or more cartridges and one or more charging components and/or one or more batteries. In further implementations, a kit may comprise a plurality of cartridges. A kit may further comprise a plurality of cartridges and one or more batteries and/or one or more charging components. In the above implementations, the cartridges or the control units may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

a housing including a power source and a control component;

a reservoir configured to contain a liquid composition;

a liquid delivery component comprising a micropump; and an atomizing assembly comprising a vibrating component and a mesh plate, wherein the micropump is configured to be controlled by the control component to deliver at least a portion of the liquid composition to the atomizing assembly, wherein the atomizing assembly is configured to be controlled by the control component to vaporize the portion of the liquid composition to generate an aerosol, and wherein the micropump and the atomizing assembly are integrated together using a common element, wherein the micropump comprises a piezoelectric micropump, wherein the vibrating component comprises a piezoelectric vibrating component, and wherein the piezoelectric micropump and the piezoelectric vibrating component are integrated together using a common piezoelectric element.

2. The aerosol delivery device of claim 1, wherein a vibrating frequency of the piezoelectric micropump is synchronized with a vibrating frequency of the piezoelectric vibrating component.

3. The aerosol delivery device of claim 1, wherein the vibrating component comprises a piezoelectric ring affixed to and substantially surrounding the mesh plate.

4. The aerosol delivery device of claim 1, wherein the mesh plate of the atomizing assembly is substantially flat.

5. The aerosol delivery device of claim 1, wherein at least a portion of the mesh plate is convex with respect to the reservoir.

6. An aerosol delivery device comprising:

a housing including a power source and a control component;

a reservoir configured to contain a liquid composition;

a liquid delivery component comprising at least a portion of a micropump; and an atomizing assembly comprising a vibrating component and a mesh plate, wherein the micropump is configured to be controlled by the control component to deliver at least a portion of the liquid composition to the atomizing assembly, and wherein the atomizing assembly is configured to be controlled by the control component to vaporize the portion of the liquid composition to generate an aerosol, and wherein the micropump comprises a biomimetic micropump, wherein the biomimetic micropump comprises a xylem model component and a leaf model component, wherein the liquid delivery component includes a first portion of the biomimetic micropump, and wherein the atomizing assembly includes a second portion of the biomimetic micropump.

7. The aerosol delivery device of claim 6, wherein the xylem model component comprises one or both of a ceramic material or a controllable material.

8. The aerosol delivery device of claim 6, wherein the leaf model component comprises a microperforated structure.

9. The aerosol delivery device of claim 6, wherein the leaf model component comprises the second portion of the biomimetic micropump.

10. The aerosol delivery device of claim 9, wherein the leaf model component comprises the mesh plate.

11. The aerosol delivery of claim 6, wherein the vibrating component comprises a piezoelectric ring affixed to and substantially surrounding the mesh plate.

12. The aerosol delivery device of claim 6, wherein the mesh plate of the vibrating assembly is substantially flat.

13. The aerosol delivery device of claim 6, wherein at least a portion of the mesh plate is convex with respect to the respective reservoir.

14. The aerosol delivery device of claim 6, wherein the leaf model component is integrated with the vibrating component of the atomizing assembly.

* * * * *

UNITED STATES PATENT AND TRADEMARK OFFICE

CERTIFICATE OF CORRECTION

PATENT NO. : 11,969,545 B2
APPLICATION NO. : 17/108628
DATED : April 30, 2024
INVENTOR(S) : Justin Dakota Holt et al.

It is certified that error appears in the above-identified patent and that said Letters Patent is hereby corrected as shown below:

On the Title Page

In Column 2, in item (56), under "Foreign Patent Documents", Line 2, delete "EE" and insert -- EP --.

In the Claims

In Column 28, the first Line of Claim 11, delete "The aerosol delivery" and insert -- The aerosol delivery device --.

Signed and Sealed this
Twentieth Day of August, 2024

Katherine Kelly Vidal

Katherine Kelly Vidal
*Director of the United States Patent and Trademark Office*